(12) United States Patent
Kim et al.

(10) Patent No.: US 9,066,837 B2
(45) Date of Patent: Jun. 30, 2015

(54) ABSORBENT ARTICLE WITH ANNULAR ABSORBENT MEMBER

(75) Inventors: Hyong Bom Kim, Uiwang-si (KR); Eun Jung Kang, Seoul (KR); Hyung Woo Park, Suwon-si (KR); Seong Dae Roh, Anyang-si (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 95 days.

(21) Appl. No.: 13/504,948

(22) PCT Filed: Oct. 29, 2010

(86) PCT No.: PCT/KR2010/007528
§ 371 (c)(1),
(2), (4) Date: Apr. 28, 2012

(87) PCT Pub. No.: WO2011/053044
PCT Pub. Date: May 5, 2011

(65) Prior Publication Data
US 2012/0277711 A1    Nov. 1, 2012

(30) Foreign Application Priority Data
Oct. 30, 2009   (KR) ................. 10-2009-0104382

(51) Int. Cl.
*A61F 13/47*   (2006.01)
*A61F 13/53*   (2006.01)
(Continued)

(52) U.S. Cl.
CPC ............ *A61F 13/535* (2013.01); *A61F 13/4756* (2013.01); *A61F 13/536* (2013.01)

(58) Field of Classification Search
CPC .................... A61F 13/49473; A61F 13/51311; A61F 2013/49493; A61F 2013/5128; A61F 13/4756; A61F 13/4757; A61F 2013/530875; A61F 2013/53734; A61F 2013/53782
USPC ................................... 604/378, 381, 385.101
See application file for complete search history.

(56) References Cited

U.S. PATENT DOCUMENTS

| | | | |
|---|---|---|---|
| 2,566,451 | A | 9/1951 | Julien |
| 2,575,165 | A | 11/1951 | Donovan |

(Continued)

FOREIGN PATENT DOCUMENTS

| | | |
|---|---|---|
| EP | 0119919 A1 | 9/1984 |
| EP | 0 164 595 A1 | 12/1985 |

(Continued)

OTHER PUBLICATIONS

PCT International Search Report for Application No. PCT/KR2010/007528.

(Continued)

*Primary Examiner* — Tan-Uyen (Jackie) T Ho
*Assistant Examiner* — Kathryn E Ditmer
(74) *Attorney, Agent, or Firm* — Dority & Manning, P.A.

(57) ABSTRACT

An absorbent article with an annular absorbent member. The absorbent article has a liquid-permeable top sheet, a liquid-impermeable back sheet, an annular absorbent member and a second absorbent member. The annular absorbent member is disposed between the top sheet and the back sheet. The annular absorbent member absorbs and retains a liquid passing through the top sheet. The annular absorbent member defines an aperture in a central portion thereof. The second absorbent member is disposed between the annular absorbent member and the back sheet. The second absorbent member has a visible area aligned with a position of the aperture of the annular absorbent member.

18 Claims, 6 Drawing Sheets

(51) Int. Cl.
  *A61F 13/535* (2006.01)
  *A61F 13/475* (2006.01)
  *A61F 13/536* (2006.01)

(56) References Cited

U.S. PATENT DOCUMENTS

| | | | |
|---|---|---|---|
| 3,073,309 A | 1/1963 | Mosier | |
| 3,343,543 A | 9/1967 | Glassman | |
| 3,441,023 A | 4/1969 | Rijssenbeek | |
| 3,545,441 A | 12/1970 | Gravdahl | |
| 3,828,786 A | 8/1974 | Cervantes | |
| 3,881,490 A | 5/1975 | Whitehead et al. | |
| 3,889,679 A | 6/1975 | Taylor | |
| 3,913,580 A | 10/1975 | Ginocchio | |
| 4,184,498 A | 1/1980 | Franco | |
| 4,285,342 A | 8/1981 | Mesek | |
| 4,337,772 A | 7/1982 | Roeder | |
| 4,375,448 A | 3/1983 | Appel et al. | |
| 4,376,799 A | 3/1983 | Tusim | |
| 4,397,644 A | 8/1983 | Matthews et al. | |
| 4,494,278 A | 1/1985 | Kroyer et al. | |
| 4,501,586 A | 2/1985 | Holtman | |
| 4,531,945 A | 7/1985 | Allison | |
| 4,556,146 A | 12/1985 | Swanson et al. | |
| 4,578,069 A | 3/1986 | Whitehead et al. | |
| 4,610,678 A | 9/1986 | Weisman et al. | |
| 4,624,666 A | 11/1986 | DeRossett et al. | |
| 4,629,643 A | 12/1986 | Curro et al. | |
| 4,631,062 A | 12/1986 | Lassen et al. | |
| 4,640,810 A | 2/1987 | Laursen et al. | |
| 4,673,403 A | 6/1987 | Lassen et al. | |
| 4,731,065 A | 3/1988 | Yamada | |
| 4,781,710 A | 11/1988 | Megison et al. | |
| 4,795,455 A | 1/1989 | Luceri et al. | |
| 4,935,022 A | 6/1990 | Lash et al. | |
| 4,988,344 A * | 1/1991 | Reising et al. | 604/368 |
| 4,988,345 A | 1/1991 | Reising | |
| 5,176,672 A | 1/1993 | Bruemmer et al. | |
| 5,188,625 A | 2/1993 | Van Iten et al. | |
| 5,252,619 A | 10/1993 | Brownscombe et al. | |
| 5,304,161 A | 4/1994 | Noel et al. | |
| 5,348,547 A | 9/1994 | Payne et al. | |
| 5,364,382 A | 11/1994 | Latimer et al. | |
| 5,366,451 A | 11/1994 | Levesque | |
| 5,382,400 A | 1/1995 | Pike et al. | |
| 5,397,316 A | 3/1995 | LaVon et al. | |
| 5,415,640 A | 5/1995 | Kirby et al. | |
| 5,462,537 A | 10/1995 | Carr et al. | |
| 5,527,171 A | 6/1996 | Soerensen | |
| 5,533,991 A | 7/1996 | Kirby et al. | |
| 5,662,633 A | 9/1997 | Doak et al. | |
| 5,692,939 A | 12/1997 | DesMarais | |
| 5,695,849 A | 12/1997 | Shawver et al. | |
| 5,743,896 A | 4/1998 | Parker | |
| 5,755,710 A | 5/1998 | Menard | |
| 5,795,344 A | 8/1998 | Chappell | |
| 5,810,798 A | 9/1998 | Finch | |
| 5,820,619 A | 10/1998 | Chen | |
| 5,830,203 A | 11/1998 | Suzuki et al. | |
| 5,843,063 A | 12/1998 | Anderson et al. | |
| 5,855,719 A | 1/1999 | Menard | |
| 5,899,893 A | 5/1999 | Dyer et al. | |
| 5,961,505 A | 10/1999 | Coe et al. | |
| 6,011,195 A * | 1/2000 | Muhs et al. | 604/367 |
| 6,059,710 A | 5/2000 | Rajala et al. | |
| 6,060,636 A | 5/2000 | Yahiaoui et al. | |
| 6,074,333 A | 6/2000 | Rajala et al. | |
| 6,075,179 A | 6/2000 | McCormack et al. | |
| 6,077,254 A | 6/2000 | Silwanowicz et al. | |
| 6,117,523 A | 9/2000 | Sugahara | |
| 6,165,306 A | 12/2000 | Rajala | |
| 6,171,432 B1 | 1/2001 | Brisebois et al. | |
| 6,241,714 B1 * | 6/2001 | Raidel et al. | 604/378 |
| D448,481 S | 9/2001 | Mok | |
| 6,284,942 B1 | 9/2001 | Rabin | |
| 6,376,095 B1 | 4/2002 | Cheung et al. | |
| 6,395,792 B1 | 5/2002 | Nagasuna et al. | |
| 6,410,823 B1 | 6/2002 | Daley et al. | |
| 6,548,732 B2 | 4/2003 | Erdman et al. | |
| 6,573,424 B1 * | 6/2003 | Raidel et al. | 604/379 |
| 6,610,903 B1 | 8/2003 | Latimer et al. | |
| D483,485 S | 12/2003 | Phillips-Nicholas | |
| 6,673,418 B1 | 1/2004 | DeOlivera et al. | |
| 6,759,567 B2 | 7/2004 | Colman et al. | |
| 6,786,893 B2 | 9/2004 | Strand | |
| 6,811,239 B1 | 11/2004 | Salacz | |
| 6,858,771 B2 * | 2/2005 | Yoshimasa et al. | 604/380 |
| 6,911,574 B1 | 6/2005 | Mizutani | |
| 6,913,599 B2 | 7/2005 | Mishima et al. | |
| 6,984,225 B2 | 1/2006 | Raidel et al. | |
| 7,037,298 B2 * | 5/2006 | Ohshima et al. | 604/385.101 |
| 7,067,711 B2 | 6/2006 | Kuroda et al. | |
| 7,145,054 B2 | 12/2006 | Zander et al. | |
| 7,156,832 B2 | 1/2007 | Drevik et al. | |
| 7,358,282 B2 | 4/2008 | Krueger et al. | |
| 7,387,620 B2 | 6/2008 | Watanabe et al. | |
| 7,402,157 B2 | 7/2008 | Christon et al. | |
| D600,798 S | 9/2009 | Hood et al. | |
| D600,799 S | 9/2009 | Hood et al. | |
| D600,800 S | 9/2009 | Hood et al. | |
| D600,802 S | 9/2009 | Hood et al. | |
| D600,804 S | 9/2009 | Hood et al. | |
| 7,594,905 B2 | 9/2009 | Tanio et al. | |
| 7,597,690 B2 | 10/2009 | Tanio et al. | |
| D612,491 S | 3/2010 | Sullivan Conrad et al. | |
| 7,686,790 B2 | 3/2010 | Rasmussen et al. | |
| 7,718,844 B2 | 5/2010 | Olson | |
| D630,316 S | 1/2011 | Hood et al. | |
| 7,976,525 B2 | 7/2011 | McDaniel | |
| 7,982,091 B2 | 7/2011 | Konawa | |
| 8,016,803 B2 | 9/2011 | Mueller et al. | |
| 8,039,685 B2 | 10/2011 | Mason, Jr. et al. | |
| 8,211,078 B2 | 7/2012 | Noel | |
| 8,293,966 B2 | 10/2012 | Obele | |
| 8,317,768 B2 | 11/2012 | Larsson | |
| 8,536,401 B2 | 9/2013 | Ecker et al. | |
| 8,541,644 B2 | 9/2013 | Raidel et al. | |
| 8,754,286 B2 | 6/2014 | Bergström et al. | |
| 2001/0044610 A1 * | 11/2001 | Kim et al. | 604/365 |
| 2003/0078553 A1 | 4/2003 | Wada et al. | |
| 2003/0125701 A1 | 7/2003 | Widlund | |
| 2003/0153232 A1 | 8/2003 | Raidel et al. | |
| 2004/0133179 A1 | 7/2004 | Steger et al. | |
| 2004/0170813 A1 * | 9/2004 | Digiacomantonio et al. | 428/195.1 |
| 2006/0287635 A1 | 12/2006 | Angel, Jr. | |
| 2007/0055210 A1 | 3/2007 | Kao | |
| 2007/0073255 A1 | 3/2007 | Thomas et al. | |
| 2007/0087169 A1 | 4/2007 | McFall | |
| 2007/0135787 A1 * | 6/2007 | Raidel et al. | 604/383 |
| 2008/0071237 A1 | 3/2008 | Chen et al. | |
| 2008/0206529 A1 * | 8/2008 | Ueminami et al. | 428/196 |
| 2008/0243100 A1 * | 10/2008 | Wu et al. | 604/385.01 |
| 2009/0209930 A1 * | 8/2009 | Hammons et al. | 604/365 |
| 2010/0174260 A1 | 7/2010 | Di Luccio et al. | |
| 2010/0256586 A1 | 10/2010 | Bergstrom et al. | |
| 2011/0060303 A1 | 3/2011 | Bissah et al. | |
| 2011/0137276 A1 * | 6/2011 | Yoshikawa | 604/378 |
| 2012/0157952 A1 | 6/2012 | Poruthoor et al. | |
| 2012/0220972 A1 | 8/2012 | Kawamura et al. | |
| 2012/0277711 A1 | 11/2012 | Kim et al. | |
| 2013/0231628 A1 | 9/2013 | Dieringer et al. | |
| 2013/0245589 A1 | 9/2013 | Toda et al. | |
| 2013/0338621 A1 | 12/2013 | Ecker et al. | |
| 2014/0128828 A1 | 5/2014 | Andersson et al. | |
| 2014/0228795 A1 | 8/2014 | Castanares et al. | |

FOREIGN PATENT DOCUMENTS

| | | |
|---|---|---|
| EP | 0 343 941 B1 | 11/1989 |
| EP | 0 769 284 A1 | 4/1997 |
| EP | 0934737 A1 * | 8/1999 |
| FR | 2 420 339 A1 | 2/2012 |
| GB | 1 349 962 | 4/1974 |

(56) References Cited

FOREIGN PATENT DOCUMENTS

| | | |
|---|---|---|
| GB | 1595393 A | 8/1981 |
| GB | 2283428 A | 5/1995 |
| GB | 2 284 767 A | 6/1995 |
| GB | 2 370 780 A | 7/2002 |
| JP | 59-85661 | 5/1984 |
| JP | 1-122727 | 8/1989 |
| JP | 06-031722 | 4/1994 |
| JP | 06-021624 | 6/1994 |
| JP | 07-012119 | 2/1995 |
| JP | 2004033325 A | 2/2004 |
| KR | 0131762 B1 | 4/1998 |
| WO | WO 9109582 A1 | 7/1991 |
| WO | WO 92/11830 | 7/1992 |
| WO | WO 97/01998 | 1/1997 |
| WO | WO 0037002 A1 | 6/2000 |
| WO | WO 0069481 A1 | 11/2000 |
| WO | WO 0069482 A1 | 11/2000 |
| WO | WO 0069483 A1 | 11/2000 |
| WO | WO 0069484 A1 | 11/2000 |
| WO | WO 0069485 A1 | 11/2000 |
| WO | WO 03015682 A1 | 2/2003 |
| WO | WO 03015684 A1 | 2/2003 |
| WO | WO 2006/105305 A1 | 10/2006 |
| WO | WO 2008146222 A1 | 12/2008 |
| WO | WO 2009/067059 | 5/2009 |
| WO | WO 2009067059 A1 | 5/2009 |
| WO | WO 2013002686 A1 | 1/2013 |
| WO | WO 2013185800 A1 | 12/2013 |

OTHER PUBLICATIONS

Translation of Japanese Patent—JPH11076304 A2, Mar. 23, 1999, 8 pages.
Abstract of Chinese Patent No. CN1066776 (A) dated Dec. 9, 1992, 2 pages.
Translation of Japanese Patent—JP59190229, 5 pages.
Abstract of Chinese Patent—CN201143260, Nov. 5, 2008, 1 page.
Abstract of Chinese Patent—CN202078469, Dec. 21, 2011, 1 page.
Abstract of Chinese Patent—CN102614049, Aug. 1, 2012, 1 page.
Abstract of Japanese Patent—JP11042250, Feb. 16, 1999, 1 page.
Abstract of Japanese Patent—JP2006051211, Feb. 23, 2006, 2 pages.
Abstract of Japanese Patent—JP2006239162, Sep. 14, 2006, 2 pages.
Abstract of Japanese Patent—JP2007050145, Mar. 1, 2007, 1 page.
Abstract of Japanese Patent—JP2009112864, Mar. 28, 2009, 1 page.

* cited by examiner (PRIOR ART)

A1                  B2

A1                  B2

A1　　　　　　　　　　　B2

A1　　　　　　　　　　　B2

A1　　　　　　B1　　　　　　B2

A1　　　　　　B1　　　　　　B2

ABSORBENT ARTICLE WITH ANNULAR ABSORBENT MEMBER

TECHNICAL FIELD

The present invention relates to an absorbent article such as a personal sanitary pad for treating menstrual blood, urinary incontinence and other bodily fluids.

BACKGROUND ART

An article such as a sanitary napkin, a panty liner and a pad for incontinence of urinary (hereinafter, referred to as "absorbent article"), which absorbs and retains bodily fluid discharged from a wearer's body, is widely known in personal sanitary art. Such an absorbent article typically includes a top sheet, a back sheet and an absorbent core disposed between the top sheet and the back sheet. The top sheet is configured to be liquid-permeable to allow the bodily fluid to permeate to the absorbent core for retaining the bodily fluid, while the back sheet is configured to be liquid-impermeable to prevent the bodily fluid from leaking out to stain a wearer's skin or undergarments.

By way of example of prior art absorbent articles, FIG. 1 shows an absorbent article disclosed in International Patent Application Publication No. WO1997/001998. FIG. 2 is a sectional view taken along the line II-II of FIG. 1. Referring to FIGS. 1 and 2, the absorbent article 50 includes a cover 52, a baffle 54, a primary absorbent member 56 and a secondary absorbent member 58. The cover 52 is liquid-permeable and is placed in contact with the wearer's body. The baffle 54 is liquid-impermeable and is attached to the wearer's undergarments. The primary absorbent member 56 serves to absorb the bodily fluid through the cover 52. The secondary absorbent member 58 is formed with an aperture 60, through which a portion of the primary absorbent member 56 is exposed.

However, in the prior art absorbent article 50 shown in FIGS. 1 and 2, the secondary absorbent member 58 includes a nonabsorbent polymeric composition of 50~95% and thus the secondary absorbent member 58 hardly contributes to spreading of the bodily fluid. That is, the spread velocity of the secondary absorbent member 58 is relatively slow. Thus, although the aperture 60 has an enough capacity to retain a large amount of the bodily fluid in an instant, the bodily fluid temporarily retained in the secondary absorbent member 58 fails to be immediately absorbed by the primary and secondary absorbent members 56, 58. As a result, the wearer may feel wet. Besides, the bodily fluid temporarily retained can leak outside of the absorbent article to stain the wearer's skin and undergarments.

DISCLOSURE OF INVENTION

The present invention is directed to solving the foregoing problems. The present invention provides an absorbent article which can appropriately treat an unexpected sudden excretion of bodily fluid.

According to various embodiments of the present invention, there is provided an absorbent article with an annular absorbent member. The absorbent article according to one embodiment may include the followings: a liquid-permeable top sheet; a liquid-impermeable back sheet; an annular absorbent member disposed between the top sheet and the back sheet for absorbing and retaining a liquid passing through the top sheet, the annular absorbent member defining an aperture in a central portion thereof, the aperture being elongated in a longitudinal direction; and a second absorbent member disposed between the annular absorbent member and the back sheet, the second absorbent member having a visible area aligned with a position of the aperture of the annular absorbent member.

In one embodiment, the second absorbent member may include: a delivering member absorbing and delivering the liquid retained in the annular absorbent member; and an absorbent body absorbing the liquid delivered through the delivering member. Further, the visible area may include a plurality of dots printed on the delivering member or a plurality of perforations defined in the delivering member.

In one embodiment, the annular absorbent member may be configured such that a lower surface of the annular absorbent member facing the second absorbent member absorbs and spreads the liquid faster than an upper surface of the annular absorbent member facing the top sheet.

In one embodiment, the annular absorbent member may have a width of 22~52 mm and a length of 50~150 mm. The annular absorbent member may have a thickness of 0.5~3 mm.

In one embodiment, the aperture may have a width of 20~50 mm and a length of 30~100 mm. An inner volume of the aperture, which is defined as a product of a planar area of the aperture and a thickness of the annular absorbent member, may be in a range of 0.5~3.0 ml. A distance from an end of the annular absorbent member in a width direction to the aperture may be equal to or more than 2 mm.

In one embodiment, the annular absorbent member may include an absorptive material being equal to or more than 50% of an entire weight of the annular absorbent member. Further, a density of the absorptive material may be lower than that of the second absorbent member. The absorptive material may include cellulosic fibers.

In one embodiment, a planar area of the aperture may be equal to or more than 20% of an entire planar area of the annular absorbent member.

In one embodiment, the aperture may include a plurality of perforations.

The absorbent article according to one embodiment includes the annular absorbent member having the aperture. Thus, the absorbent article can instantly absorb and retain a large amount of bodily fluid and can deliver the bodily fluid to the absorbent body through the delivering member. Since the top sheet is partially spaced apart from the delivering member via the aperture of the annular absorbent member, the top sheet can dry in a shorter amount of time after introduction of the bodily fluid. Accordingly, the absorbent article can provide a dry feel to a wearer.

Since the aperture is elongatedly formed in the longitudinal direction of the absorbent article in the central portion of the annular absorbent member, the bodily fluid passing through the top sheet can predominately spread in the longitudinal direction rather than the width direction of the absorbent article. Accordingly, it is possible to prevent the bodily fluid from heavily spreading in the width direction of the absorbent article thereby leaking out in the width direction of the absorbent article.

Further, since the visible area is formed in the delivering member so as to correspond to the aperture of the annular absorbent member, the wearer may visibly see the visible area through the top sheet. As a result, the wearer may believe that a capacity of the aperture is greater than the actual capacity and can expect that the absorbent article instantly absorbs a large amount of the bodily fluid. Thus, the absorbent article can provide a safe feel to the wearer.

BEST MODE FOR CARRYING OUT THE INVENTION

Figure 1:
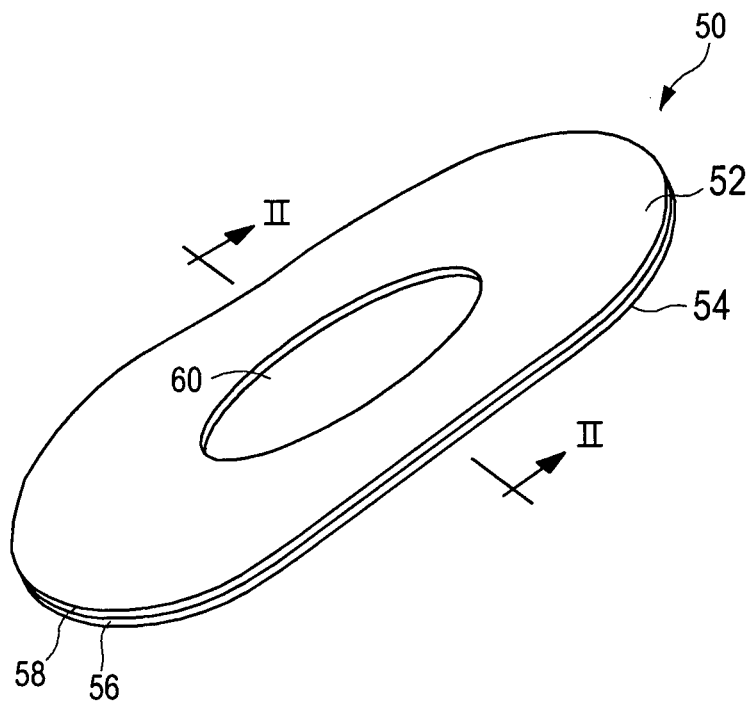
FIG. 1 is a perspective view showing a prior art absorbent article.
Figure 2:
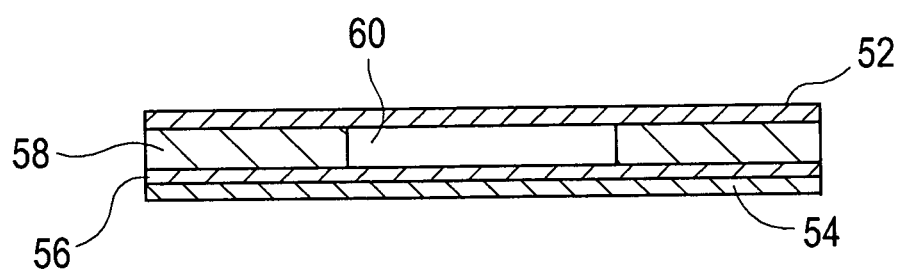
FIG. 2 is a sectional view taken along the line II-II of FIG. 1.

Embodiments of an absorbent article will now be described below with reference to the accompanying drawings. Like reference numerals indicate like or corresponding parts throughout the views of the drawings.

As used herein, the term "longitudinal direction" generally refers to a direction that coincides with a forward and backward direction in a wearer's body when the absorbent article is fitted to a wearer, while the term "width direction" refers to a direction orthogonal to the longitudinal direction. Further, as used herein, the term "upper" is generally based on the orientation depicted in the figures, while the term "lower" generally refers to a direction opposite to the upper direction.

Figure 3:
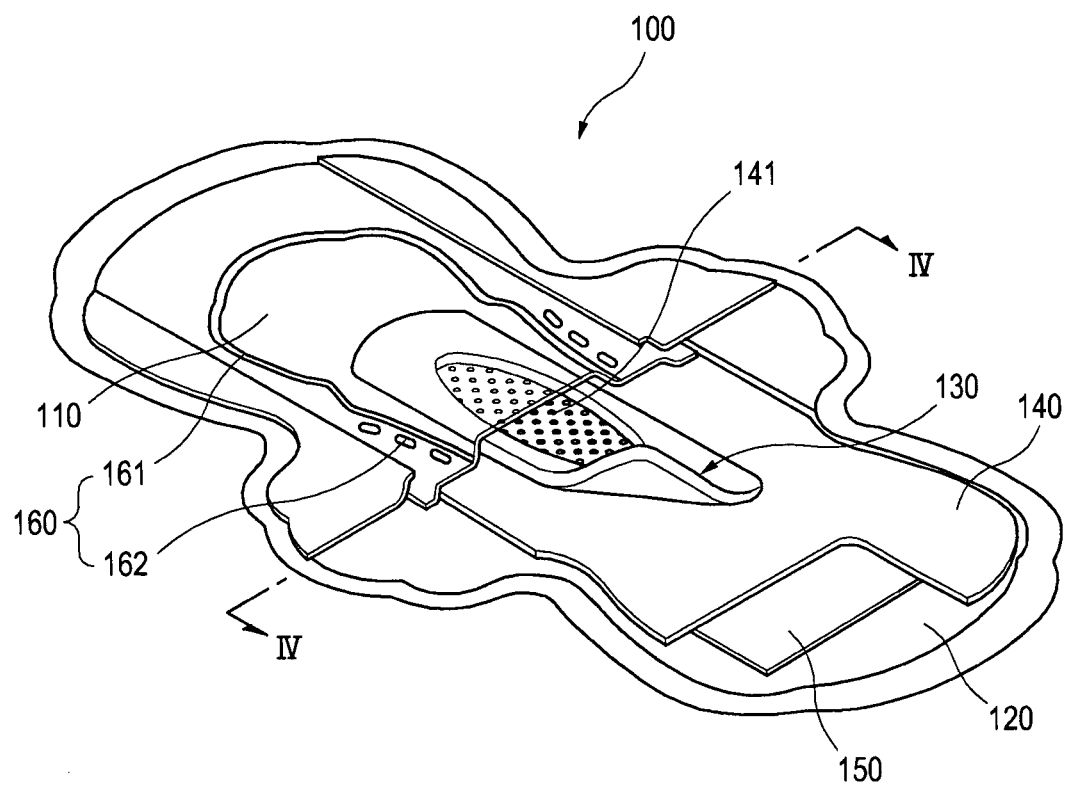
FIG. 3 is a perspective view showing an absorbent article according to one embodiment with parts of the absorbent article partially cut away.
Figure 4:
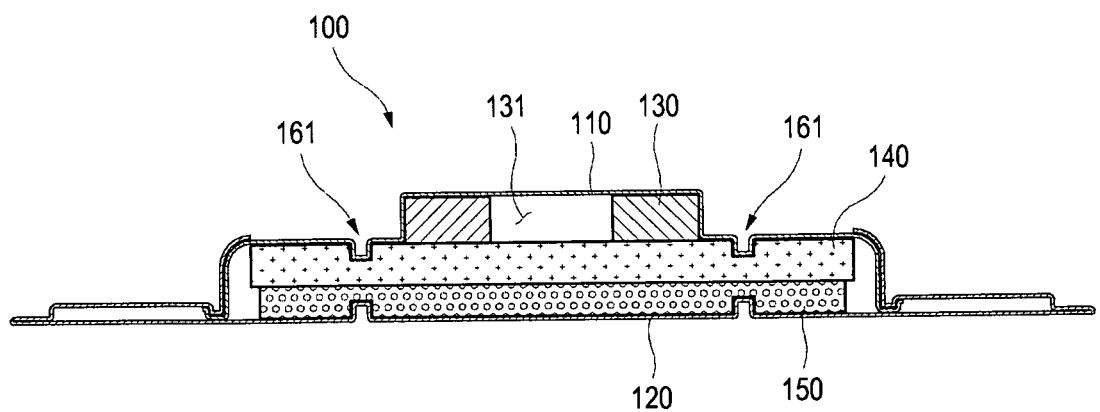
FIG. 4 is a sectional view taken along the line IV-IV of FIG. 3.
Figure 5:
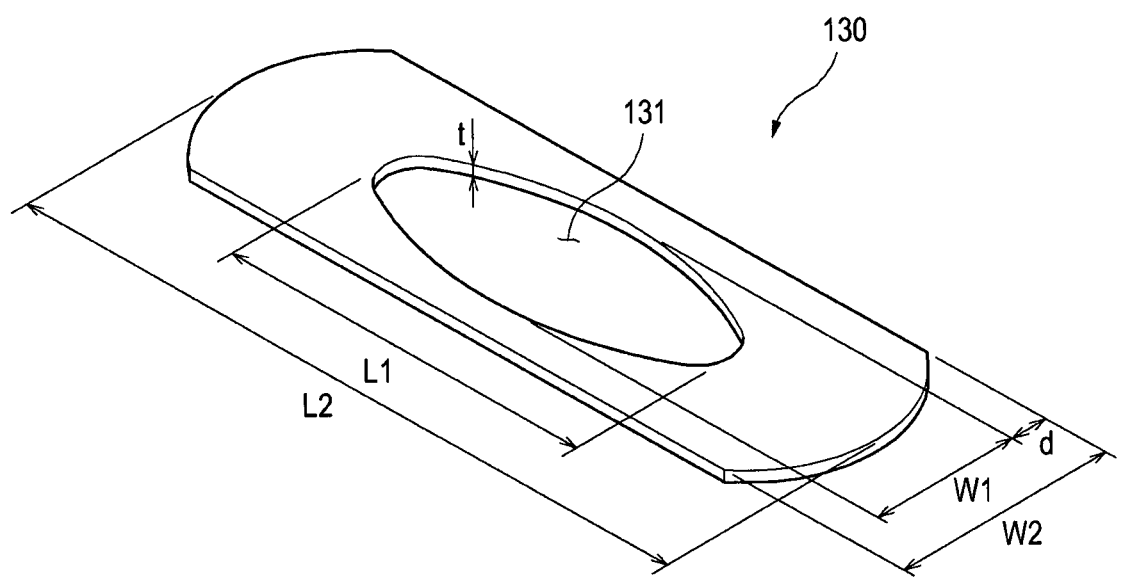
FIG. 5 is perspective view showing an annular absorbent member shown in FIG. 3.

Referring to FIGS. 3 to 5, the absorbent article 100 according to one embodiment of the present invention includes: a liquid-permeable top sheet 110; a liquid-impermeable back sheet 120; and an annular absorbent member 130 and a second absorbent member 140, 150 disposed between the top sheet 110 and the back sheet 120. The second absorbent member 140, 150 is disposed between the annular absorbent member 130 and the back sheet 120. The annular absorbent member 130 absorbs and retains a liquid passing through the top sheet 110. The annular absorbent member 130 has an aperture 131 defined in a central portion thereof. The aperture 131 is elongatedly formed in a longitudinal direction. The second absorbent member has a visible area or recognition area 141 that is aligned with the aperture 131 of the annular absorbent member 130. In one embodiment, the second absorbent member 140, 150 may include: a delivering member 140 absorbing and delivering the liquid retained within the annular absorbent member 130; and an absorbent body 150 absorbing and collecting the liquid delivered through the delivering member 140 therein. The delivering member 140 and the absorbing body 150 may be separately configured or integrally formed. The liquid may include a fluid discharged from a wearer's body (hereinafter bodily fluid).

The top sheet 110 serves to pass the liquid therethrough and rapidly move the liquid to the annular absorbent body 130 that is in contact with the top sheet 110. The top sheet 110 may include a material having wettability, hydrophilicity and porosity.

The back sheet 120 may be made from a liquid-impermeable polyethylene film. The back sheet 120 prevents the bodily fluid retained in the absorbent body 150 from externally leaking or oozing out to spot or stain a wearer's skin or undergarments.

The annular absorbent member 130 is disposed beneath the top sheet 110. The annular absorbent member 130 serves to absorb a part of the bodily fluid passing or permeating through the top sheet 110 and to temporarily retain the same.

As shown in FIG. 5, the single aperture 131 is defined at the central portion of the annular absorbent member 130. In another embodiment, the annular absorbent member 130 may include a plurality of perforations, which are arranged to correspond to the shape of the aperture 131, instead of the single aperture 131. The aperture 131 may contribute to increase the volume the annular absorbent member 130 can temporarily retain. Since the top sheet 110 and the delivering member 140 are spaced apart from each other via the aperture 131, the absorbent article 100 can provide a dry feel to a wearer. In one embodiment, a width W1 of the aperture 131 may be in a range of 20~50 mm and a length L1 of the aperture 131 may be in a range of 30~100 mm. Further, a width W2 of the annular absorbent member 130 may be in a range of 22~52 mm, while a length L2 of the annular absorbent member 130 may be in a range of 50~150 mm. To provide a physical barrier to the annular absorbent member 130, a distance d between an end or edge in a width direction of the annular absorbent member 130 and the aperture 131 may be equal to or more than 2 mm.

When the aperture 131 is elongatedly formed in the longitudinal direction of the absorbent article 100, the bodily fluid predominately tends to be absorbed and spread in the longitudinal direction rather than a width direction of the absorbent article 100. Accordingly, it is possible to prevent the bodily fluid from heavily spreading in the width direction of the absorbent article 100 thereby leaking out of the absorbent article 100. In one embodiment, a thickness t of the aperture 131 (e.g., a thickness of the annular absorbent member 130) may be in a range of 0.5~3 mm. Further, an inner volume of the aperture 131, which can be defined as the product of a planar area of the aperture 131 and the thickness t of the aperture 131, may be in a range of 0.5~2.0 ml. Thus, the annular absorbent member 130 can temporarily retain a large amount of the bodily fluid.

In one embodiment, the annular absorbent member 130 may include a single hydrophilic material, a single hydrophobic material and a composite thereof. Further, the annular absorbent member 130 may comprise an absorptive material more than 50% of an entire weight of the annular absorbent member 130. In some embodiments, the absorptive material may include cellulosic fibers. The absorptive material may have a density lower than that of the delivering member 140 or the absorbent body 150. The annular absorbent member 130 in some embodiments is configured such that a lower surface of the annular absorbent member 130 facing the delivering member 140 absorbs and spreads the bodily fluid faster than an upper surface of the annular absorbent member 130 facing the top sheet 110.

The aperture 131 of the annular absorbent member 130 allows the bodily fluid to pass through the top sheet 110 to be quickly absorbed into the absorbent body 150. Thus, Further, it is possible to prevent the bodily fluid from leaking or oozing outwardly of the delivering member 140 before the bodily fluid is absorbed by the absorbent body 150. That is, the annular absorbent member 130 can serve as the physical barrier for the bodily fluid. The annular absorbent member 130 can ensure flexibility of the absorbent article 100 and maintain an original shape of the absorbent article 100. To this end, in some embodiments the planar area of the aperture 131 is equal to or more than 20% of an entire planar area of the annular absorbent member 130. The annular absorbent member 130 may have a rectangular shape with a rectangular aperture according to a design of the absorbent article.

The delivering member 140 not only delivers the bodily fluid retained within the annular absorbent member 130 toward the absorbent body 150, but absorbs a part of the bodily fluid at the same time. The delivering member 140 may include a visible area (or a recognition area) 141 that is formed to correspond to the shape of the aperture 131 of the annular absorbent member 130, that is aligned with the position of the aperture 131.

In one embodiment, the visible area 141 may include a plurality of dots printed on the upper surface of the delivering member 140. Further, the visible area 141 may include a plurality of perforations (or small holes) formed in the delivering member 140. As shown in FIG. 3, the plurality of the dots or the plurality of the perforations may be arranged to match or correspond to the shape of the aperture 131. If the visible area includes dots, such dots may be printed with a color deeper than the top sheet (110) or the delivering member 140. If the dots with a deeper color are seen through the top sheet 110 together with the aperture 131, the wearer may believe that the depth of the aperture 131 (or a height of the annular absorbent member 130) is greater than an actual depth or height. Therefore, the wearer can expect that the aperture 131 has great capacity and the absorbent article absorbs a large amount of the bodily fluid. Thus, the wearer can feel safe. Further, as for the visible area 141 including the perforations, the wearer may believe that the capacity of the aperture 131 seen through the top sheet 110 has a greater capacity and therefore can feel safe. Moreover, the perforations can substantially increase the capacity of the aperture 131. As a result, the body fluid retained in both the aperture 131 and the perforations can be quickly delivered to the absorbent body 150. In other embodiments, the visible area 141 may include various patterns to enhance an aesthetic feel of the absorbent article 100.

The absorbent body 150 is disposed between the delivering member 140 and the back sheet 120 to quickly absorb and collect the bodily fluid therein. The absorbent body 150 may include a material that is compressive, compliable and non-stimulating to the wearer's skin.

In one embodiment, the absorbent article 100 may further include an embossing portion 160 for effectively preventing coagulation and leakage of bodily fluid. The embossing portion 160 may be formed by pressing the top sheet 110, the delivering member 140 and the absorbent body 150. The embossing portion 160 may include: a first embossing portion 161 positioned alongside the delivering member 140 and the absorbent body 150; and a second embossing portion 162 adjacent to the first embossing portion 161 in the longitudinal direction of the absorbent article 100. The first embossing portion 161 may have a looped curve shape and the second embossing portion 162 may have the shape of discontinuous dots.

Next, descriptions will be made on the performance of the absorbent article according to one embodiment based on the results of the tests conducted together with absorbent articles according to a comparative example. Artificial blood was used in the tests as liquid to be absorbed by the absorbent articles. Blood of animals such as an ox or a horse may be used as the liquid to be absorbed.

Absorption Time

Table 1 provided below shows the absorption time when artificial blood is loaded on different kinds of absorbent articles under the same conditions.

TABLE 1

|  | A1 | B1 | B2 |
|---|---|---|---|
| Absorption time (sec) | 14.5 | 27.6 | 37.2 |

A1: Absorbent article according to one embodiment
B1: Comparative example 1
B2: Comparative example 2 (Absorbent article of another company)

It can be seen from Table 1 that the absorption time in the absorbent article (A1) according to one embodiment decreased about 30~50% when compared to comparative examples 1 and 2 (B1, B2).

Change in Absorption Time Associated with Repetitively Loading

Table 2 provided below shows the absorption time when 3 ml of artificial blood is loaded three times on different kinds of absorbent articles under the same conditions.

TABLE 2

|  | A1 | B1 |
|---|---|---|
| First absorption time (sec) | 4.6 | 5.7 |
| Second absorption time (sec) | 4.3 | 11.1 |
| Third absorption time (sec) | 9.7 | 16.6 |

A1: Absorbent article according to one embodiment
B1: Comparative example 1

As for comparative example 1, the second and third absorption times increased about two times and about three times in comparison with the first absorption time. By contrast, in the absorbent article (A1) according to one embodiment, the second absorption time was almost equal to the first absorption time. In addition, the third absorption time increased about two times in comparison with the first or second absorption time. Accordingly, although the artificial blood is repetitively loaded on the absorbent article (A1), the absorption time in the absorbent article (A1) did not increase significantly.

Function of Annular Absorbent Member as a Physical Barrier

Figure 6:
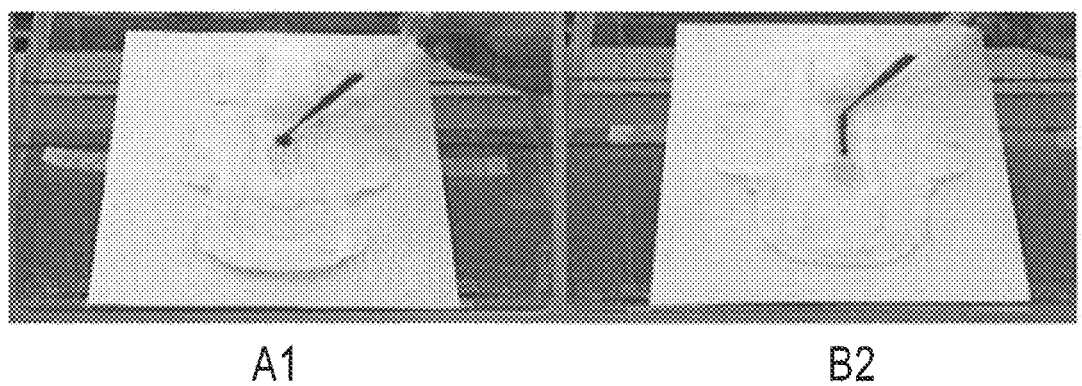
FIG. 6 is a photograph showing artificial blood loaded on an absorbent article tilted in a longitudinal direction.
Figure 7:
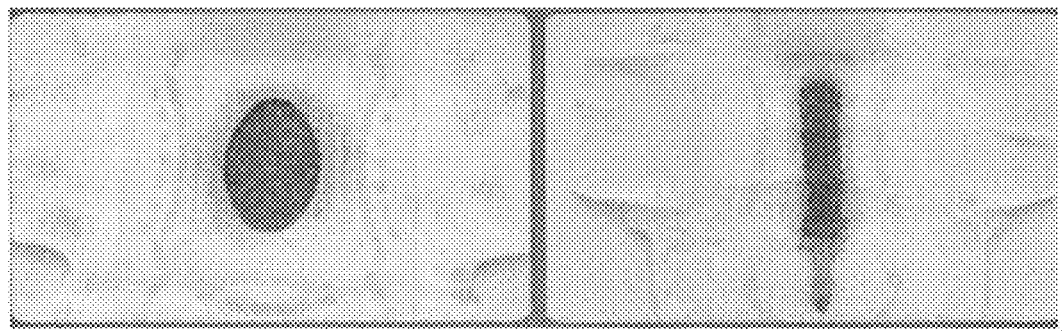
FIG. 7 is a photograph showing artificial blood spreading after being loaded as shown in FIG. 6.
Figure 8:
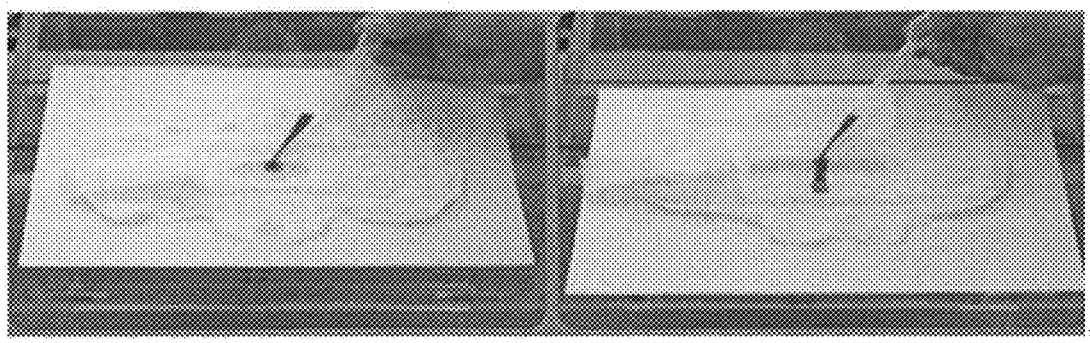
FIG. 8 is a photograph showing artificial blood loaded on an absorbent article tilted in a width direction.
Figure 9:
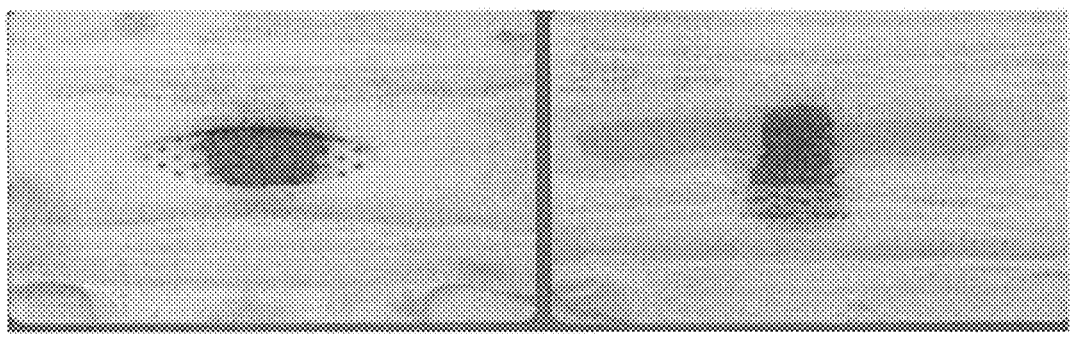
FIG. 9 is a photograph showing artificial blood spreading after loading as shown in FIG. 8.

FIG. 6 illustrates that artificial blood is loaded on the absorbent article and tilted in the longitudinal direction. FIG. 7 illustrates that the artificial blood spreads after being loaded as shown in FIG. 6. FIG. 8 illustrates artificial blood being loaded on the absorbent article tilted in the width direction. FIG. 9 illustrates artificial blood spreading after being loading as shown in FIG. 8.

In FIGS. 6 and 7, the artificial blood was loaded on the absorbent article which was tilted at about 30 degrees in the longitudinal direction of the absorbent articles. As clearly can be seen from the comparison in FIG. 7, in comparative example 2 (B2), the artificial blood flowed down in a tilt direction of the absorbent article after being loaded. However, very little artificial blood in the absorbent article (A1) according to one embodiment flowed outward of the aperture of the annular absorbent member.

Referring to FIGS. 8 and 9, the artificial blood was loaded on the absorbent article which was tilted at about 30 degrees in the width direction of the absorbent articles. As clear from the comparison in FIG. 9, in comparative example 2 (B2), the artificial blood flowed down in a tilt direction of the absorbent article after loading. However, very little artificial blood in the absorbent article (A1) according to one embodiment flowed outward of the aperture of the annular absorbent member.

Accordingly, it is ascertained that the annular absorbent member of the absorbent article according to one embodiment functions as a physical barrier.

Flexibility of Absorbent Article

Table 3 provided below shows forces required to deform different kinds of absorbent articles under the same conditions.

TABLE 3

|  | A1 | B1 |
|---|---|---|
| Force required to deform absorbent article (g · f) | 6.84 | 19.60 |

A1: Absorbent article with annular absorbent member according to one embodiment
B1: Comparative example 1

The force required to deform the absorbent article (A1) according to one embodiment decreased by about 50% when compared to that of comparative example 1 (B1). That is, the flexibility of the absorbent article (A1) increased by about 50% when compared to that of the comparative example 1 (B1). Accordingly, when a wearer moves or acts actively while wearing the absorbent article, such flexibility of the absorbent article can provide a close fit to the wearer.

Spreading of Artificial Blood in an Absorbent Article

Figure 10:
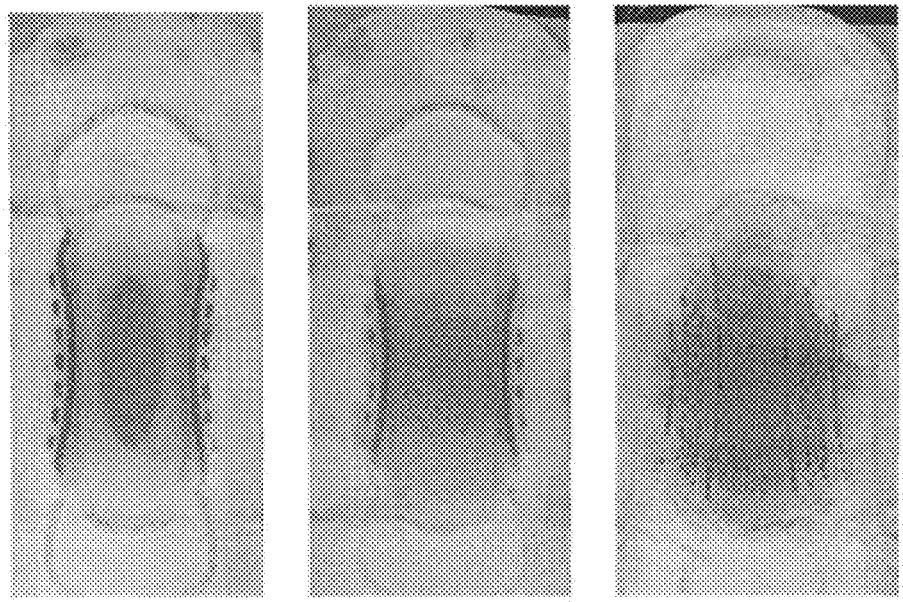
FIG. 10 is a photograph showing a top sheet after artificial blood is loaded on an absorbent article.
Figure 11:
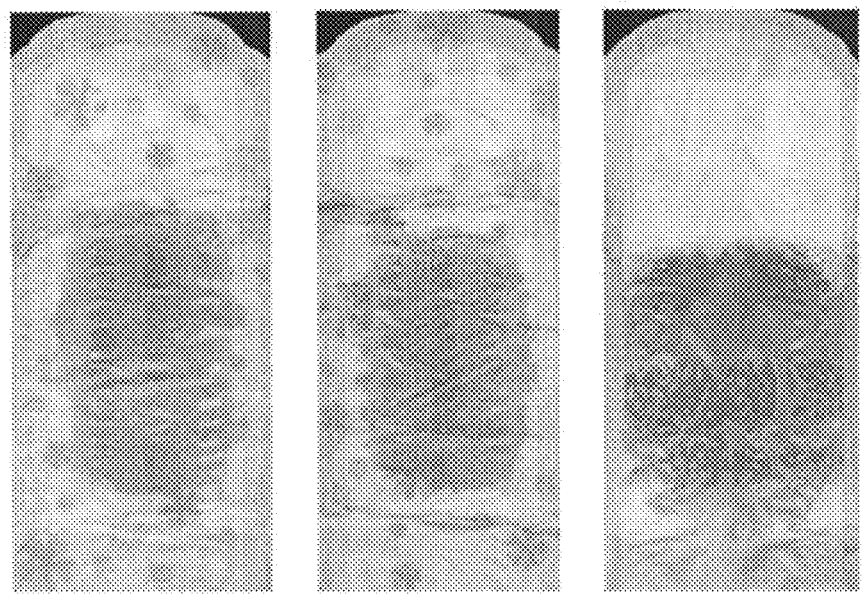
FIG. 11 is a photograph showing a back sheet after artificial blood is loaded on an absorbent article.

FIG. 10 illustrates the top sheets of the absorbent articles after loading of the artificial blood. FIG. 11 illustrates the back sheets of the absorbent articles after loading of the artificial blood.

As illustrated in FIGS. 10 and 11, the artificial blood in comparative examples 1 and 2 (B1, B2) spread in both the longitudinal direction and the width direction of the respective absorbent articles. Further, in comparative examples 1 and 2 (B1, B2), the extent of spreading in the longitudinal direction of the absorbent article was nearly equal to that in the width direction. In particular, the artificial blood in comparative example 2 (B2) spread up to both ends of the absorbent article in the width direction. In the absorbent article (A1) according to one embodiment, however, the artificial blood predominately spread in the longitudinal direction rather than the width direction. That is, in the absorbent article (A1) according to one embodiment, bodily fluid can maximally spread toward both ends of the delivering member and the absorbent body in the longitudinal direction. Accordingly, the absorbent article (A1) according to one embodiment can reduce the absorption time and increase the absorption capacity. Further, the absorbent article (A1) according to one embodiment can prevent bodily fluid from heavily spreading in the width direction of the absorbent article to leaking out in the width direction of the absorbent article.

While the present invention has been shown and described by way of the foregoing embodiments, the present invention should not be limited thereto. It will be apparent to those of ordinary skill in the art that various alternations or modifications may be made without departing from the scope of the present invention.

The invention claimed is:

1. An absorbent article comprising: a liquid permeable top sheet; a liquid impermeable back sheet; an annular absorbent member disposed between the top sheet and the back sheet capable of absorbing and retaining liquid passing through the top sheet, the annular absorbent member having a longitudinally elongated aperture in a central portion thereof; a second absorbent member disposed between the annular absorbent member and the back sheet, wherein the second absorbent member comprises: a delivering member for absorbing and delivering the liquid retained in the annular absorbent member, and a separate absorbent body for absorbing the liquid delivered through the delivering member; the second absorbent member having a visible area aligned with a position of said aperture of the annular absorbent member, wherein the visible area includes a printed pattern printed on the delivering member; and wherein the second absorbent member further comprises an embossing portion, wherein the embossing portion at least partially surrounds the annular absorbent member.

2. The absorbent article of claim 1, wherein the annular absorbent member is configured such that a lower surface of the annular absorbent member facing the second absorbent member absorbs and spreads the liquid faster than an upper surface of the annular absorbent member facing the top sheet.

3. The absorbent article of claim 1, wherein the annular absorbent member has a width of 22~52 mm and a length of 50~150 mm.

4. The absorbent article of claim 1, wherein the annular absorbent member has a thickness of 0.5~3 mm.

5. The absorbent article of claim 1, wherein the aperture has a width of 20~50 mm and a length of 30~100 mm.

6. The absorbent article of claim 1, wherein an inner volume of the aperture is in a range of 0.5~3.0 ml, the inner volume being defined as a product of a planar area of the aperture and a thickness of the annular absorbent member.

7. The absorbent article of claim 1, wherein a distance from an end of the annular absorbent member in a width direction to the aperture is equal to or greater than 2 mm.

8. The absorbent article of claim 1, wherein the annular absorbent member comprises an absorptive material being equal to or greater than 50% of an entire weight of the annular absorbent member.

9. The absorbent article of claim 8, wherein a density of the absorptive material is lower than that of the second absorbent member.

10. The absorbent article of claim 8, wherein the absorptive material comprises cellulosic fibers.

11. The absorbent article of claim 1, wherein a planar area of the aperture is equal to or greater than 20% of an entire planar area of the annular absorbent member.

12. The absorbent article of claim 1, wherein the visible area is formed to correspond to the shape of the aperture of the annular absorbent member.

13. The absorbent article of claim 1, wherein the printed pattern includes a plurality of dots.

14. The absorbent article of claim 1, wherein the visible area includes a perforated pattern.

15. The absorbent article of claim 14, wherein the perforated pattern includes a plurality of perforations.

16. The absorbent article of claim 1, wherein the embossing portion compresses the top sheet and the delivering member.

17. The absorbent article of claim 16, wherein the embossing portion further compresses the absorbent body.

18. The absorbent article of claim 1, wherein the embossing portion surrounds the annular absorbent member.

* * * * *

UNITED STATES PATENT AND TRADEMARK OFFICE
CERTIFICATE OF CORRECTION

PATENT NO.       : 9,066,837 B2                          Page 1 of 1
APPLICATION NO.  : 13/504948
DATED            : June 30, 2015
INVENTOR(S)      : Hyong Bom Kim et al.

It is certified that error appears in the above-identified patent and that said Letters Patent is hereby corrected as shown below:

On the Title Page

Item (73), "Kimberly-Clark Worldwide, Inc., Neenah, WI (US)" should read --Yuhan-Kimberly, Limited, Seoul, Republic of Korea (KR)--

Signed and Sealed this
First Day of January, 2019

Andrei Iancu
*Director of the United States Patent and Trademark Office*